United States Patent
Yu et al.

(10) Patent No.: US 12,221,461 B2
(45) Date of Patent: *Feb. 11, 2025

(54) SAPONIN ADJUVANT AND EVALUATION METHOD THEREOF

(71) Applicant: OBI PHARMA, INC., Taipei (TW)

(72) Inventors: Cheng-Der Tony Yu, Taipei (TW); Yih-Huang Hsieh, Taipei (TW); Wei Han Lee, Taipei (TW); Yu Chen Lin, Taipei (TW); Nan Hsuan Wang, Taipei (TW)

(73) Assignee: OBI PHARMA, INC., Taipei (TW)

( * ) Notice: Subject to any disclaimer, the term of this patent is extended or adjusted under 35 U.S.C. 154(b) by 1176 days.

This patent is subject to a terminal disclaimer.

(21) Appl. No.: 17/041,175

(22) PCT Filed: Mar. 27, 2019

(86) PCT No.: PCT/US2019/024414
§ 371 (c)(1),
(2) Date: Sep. 24, 2020

(87) PCT Pub. No.: WO2019/191317
PCT Pub. Date: Oct. 3, 2019

(65) Prior Publication Data
US 2021/0024569 A1  Jan. 28, 2021

Related U.S. Application Data

(60) Provisional application No. 62/649,091, filed on Mar. 28, 2018.

(51) Int. Cl.
| | | |
|---|---|---|
| *C07J 63/00* | (2006.01) | |
| *A61K 39/39* | (2006.01) | |
| *G01N 30/14* | (2006.01) | |
| *G01N 30/60* | (2006.01) | |
| *G01N 30/74* | (2006.01) | |
| *G01N 30/86* | (2006.01) | |
| *G01N 33/15* | (2006.01) | |
| *A61K 39/00* | (2006.01) | |
| *G01N 30/02* | (2006.01) | |

(52) U.S. Cl.
CPC ............ *C07J 63/008* (2013.01); *A61K 39/39* (2013.01); *G01N 30/14* (2013.01); *G01N 30/60* (2013.01); *G01N 30/74* (2013.01); *G01N 30/8631* (2013.01); *G01N 30/8675* (2013.01); *G01N 33/15* (2013.01); *A61K 2039/55577* (2013.01); *G01N 2030/027* (2013.01)

(58) Field of Classification Search
None
See application file for complete search history.

(56) References Cited

U.S. PATENT DOCUMENTS

| | | |
|---|---|---|
| 6,524,584 B2 | 2/2003 | Kensil |
| 2017/0065715 A1 | 3/2017 | Vandepapeliere |
| 2018/0028629 A1* | 2/2018 | Yu ..................... A61K 39/0011 |

OTHER PUBLICATIONS

Nord et al., "Separation and structural analysis of saponins in a bark extract from Quillaja saponaria Molina," Carbohydrate Research 320 (1999): 70-81.
Nyberg et al., "Solid-phase extraction NMR studies of chromatographic fractions of saponins from Quillaja saponaria," Analytical Chemistry, vol. 75, No. 2, Jan. 15, 2003: 268-274.
Kite et al., "Metabolomic analysis of saponins in crude extracts of Quillaja Saponaria by liquid chromatography/mass spectrometry for product authentication," Rapid Communications in Mass Spectrometry, 2004; 18: 2859-2870.
Cleland et al., "Isomerization and formulation stability of the vaccine adjuvant QS-21," Journal of Pharmaceutical Sciences vol. 85, No. 1, Jan. 1996.
Jacobsen et al., "Structure of the saponin adjuvant QS-21 and its base-catalyzed isomerization product by $_1$H and natural abundance $_{13}$C NMR spectroscopy," Carbohydrate Research 280 (1996): 1-14.
Soltysik et al., "Adjuvant activity of QS-21 isomers," Annals of the New York Academy of Sciences vol. 690, Issue 1, Aug. 1993: 392-395.
International Search Report for PCT Patent App. No. PCT/US2019/024414 (Jul. 26, 2019).

* cited by examiner

*Primary Examiner* — Dale R Miller
(74) *Attorney, Agent, or Firm* — Birch, Stewart, Kolasch & Birch, LLP

(57) ABSTRACT

The present disclosure is related to the six isomer structures (OBI-821-1990-V1A, OBI-821-1990-V1B, OBI-821-1990-V2A, OBI-821-1990-V2B, OBI-821-1858-A, and OBI-821-1858-B) of isolated OBI-821 adjuvant and the method for evaluating the quality thereof. The method of the present disclosure adopts hydrophilic interaction liquid chromatography (HILIC) and reverse phase high performance liquid chromatography (RP-HPLC) either alone or in tandem and is able to separate the isomers of OBI-821 adjuvant in the consequent chromatography. Accordingly, the quality of OBI-821 adjuvant can be further evaluated.

15 Claims, 6 Drawing Sheets

SAPONIN ADJUVANT AND EVALUATION METHOD THEREOF

CROSS-REFERENCE TO RELATED APPLICATIONS

This application is a national phase entry under 35 U.S.C. § 371 of PCT Patent Application No. PCT/US2019/024414, filed on Mar. 27, 2019, which claims priority under 35 U.S.C. § 119 from U.S. Provisional Patent Application Ser. No. 62/649,091, filed Mar. 28, 2018 and entitled "NOVEL SAPONIN ADJUVANT," both of which are hereby incorporated herein by reference in its entirety for all purposes.

TECHNICAL FIELD

The present disclosure discloses a saponin based adjuvant derived from the bark of the *Quillaja saponaria* Molina tree. It is a purified saponin adjuvant structurally similar to the descriptions found for another adjuvant, QS-21. Furthermore, the present disclosure discloses a method for evaluating the quality of saponins by high performance liquid chromatography.

BACKGROUND

Saponin is a type of compound extracted from *Quillaja Saponaria* Molina bark. Previous study showed several saponins, designated as QS-7, QS-17, QS-18, and QS-21, are able to dramatically boost antibody levels, which implied their pharmaceutical application as adjuvant (Charlotte R. Kensil et al., *The Journal of Immunology*, Vol. 146, No. 02, page 431-437, 1991). Among them, QS-21 has been practically and widely used as adjuvant in vaccines.

SUMMARY

In light of the foregoing, the objective of the present disclosure is to disclose the six isomers of a saponin based adjuvant and the methods to separate these isomers so that the purity and/or quality thereof can be further evaluated.

Another objectives of the present disclosure is to provide isolated saponin compound from a saponin based adjuvant so that the pharmaceutical use can be evaluated and fulfilled.

In order to achieve the aforesaid objectives, the present disclosure provides an isolated compound of formula (I)

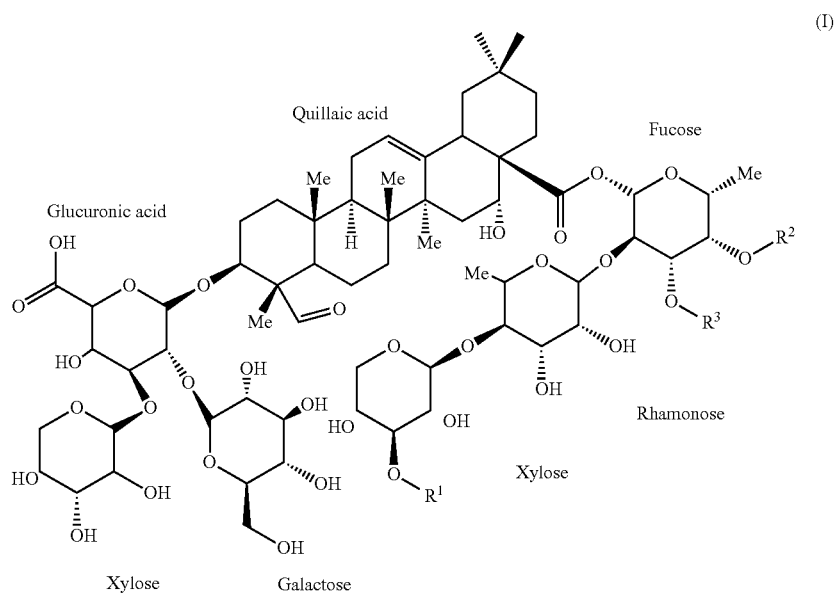

or a pharmaceutically acceptable salt thereof, wherein,
R$^1$ is selected from β-D-Apiose, β-D-Xylose or hydrogen; and
R$^2$ and R$^3$ are selected from hydrogen or

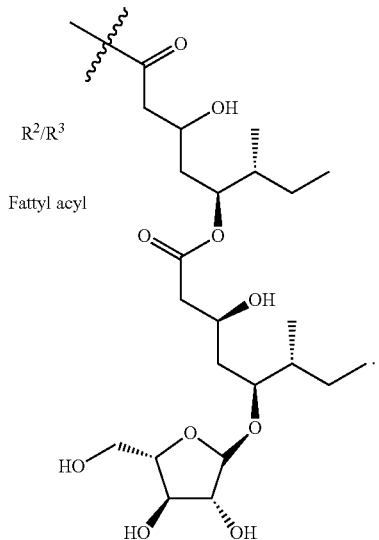

R$^2$/R$^3$

Fattyl acyl

Preferably, said isolated compound has a structure as showed in the following table:

| Reference Name | R$^1$ | | R$^2$ | R$^3$ |
| --- | --- | --- | --- | --- |
| Compound 1990-V1A | β-D-Apiose | (1) | Fatty acyl | H |
| Compound 1990-V1B | β-D-Apiose | (1) | H | Fatty acyl |
| Compound 1990-V2A | β-D-Xylose | (2) | Fatty acyl | H |
| Compound 1990-V2B | β-D-Xylose | (2) | H | Fatty acyl |
| Compound 1858-A | H | (3) | Fatty acyl | H |
| Compound 1858-B | H | (3) | H | Fatty acyl | wherein R$^1$ is apiose, xylose, or H;
wherein R$^2$ and R$^3$ are independently hydrogen or a fatty acyl.

The present disclosure also provides a saponin composition, comprising one or more of the aforesaid isolated compound and a pharmaceutical acceptable carrier.

The present disclosure more provides a method for evaluating the isomer composition of a saponin composition, comprising: (a) applying the saponin composition to a hydrophilic interaction liquid chromatography (HILIC) column; (b) eluting said hydrophilic interaction liquid chromatography (HILIC) column with a mobile phase to obtain an eluate; and (c) obtaining a chromatogram of said eluate; wherein said mobile phase comprises a trifluoroacetic acid-water solution and acetonitrile; wherein the amount of said trifluoroacetic acid-water solution in said mobile phase varies from 0% (v/v) to 20% (v/v) while the amount of said acetonitrile in said mobile phase varies from 80% (v/v) to 100% (v/v) in 30 minutes; wherein said % (v/v) is based on the total volume of said mobile phase.

Preferably, said eluting is conducted at a flow rate of 0.1 to 10 mL/min.

Preferably, said eluting is conducted at a pH range of 2 to 11.

Preferably, said hydrophilic interaction liquid chromatography (HILIC) column is an amide column.

Preferably, said chromatogram is obtained by ultraviolet detection.

The present disclosure further provides a method for evaluating the purity of a saponin composition, comprising: (a) applying a the saponin composition to a reverse phase high performance liquid chromatography (RP-HPLC) column; (b) eluting said reverse phase high performance liquid chromatography (RP-HPLC) column with a mobile phase to obtain an eluate; and (c) obtaining a chromatogram of said eluate; wherein said mobile phase comprises a trifluoroacetic acid-water solution and a trifluoroacetic acid-acetonitrile solution; wherein said trifluoroacetic acid-acetonitrile solution comprises 20 to 80% (v/v) of said trifluoroacetic acid based on the total volume of said trifluoroacetic acid-acetonitrile solution; while the amount of said acetonitrile in said mobile phase varies from 20% (v/v) to 80% (v/v) in 35 minutes; wherein said % (v/v) is based on the total volume of said mobile phase.

Preferably, said eluting is conducted at a flow rate of 0.1 to 10 mL/min.

Preferably, said eluting is conducted at a pH range of 2 to 7.5.

Preferably, said reverse phase high performance liquid chromatography (RP-HPLC) column is a reverse phase column.

Preferably, said hydrophobic column is a C4 column, C8 column, or C18 column.

Preferably, said chromatogram is obtained by ultraviolet detection.

The present disclosure more provides a method for evaluating the quality of a saponin composition, comprising: (a) applying the saponin composition to a hydrophilic interaction liquid chromatography (HILIC) column; (b) eluting said hydrophilic interaction liquid chromatography (HILIC) column with a first mobile phase to collect a first eluate; (c) applying a fraction of said first eluate to a reverse phase high performance liquid chromatography (RP-HPLC) column; (d) eluting said reverse phase high performance liquid chromatography (RP-HPLC) column with a second mobile phase to collect a second eluate; and (e) obtaining a chromatogram of said second eluate; wherein said first mobile phase comprises a trifluoroacetic acid-water solution and acetonitrile.

Preferably, the amount of said trifluoroacetic acid-water solution in said first mobile phase varies from 0% (v/v) to 20% (v/v) while the amount of said acetonitrile in said first mobile phase varies from 80% (v/v) to 100% (v/v) in 30 minutes; wherein said % (v/v) is based on the total volume of said first mobile phase;

Preferably, the amount of said trifluoroacetic acid-water solution in said second mobile phase varies from 20% (v/v) to 80% (v/v) while the amount of said acetonitrile in said second mobile phase varies from 20% (v/v) to 80% (v/v) in 35 minutes; wherein said % (v/v) is based on the total volume of said second mobile phase.

Preferably, said eluting in said step (b) is conducted at a flow rate of 0.1 to 10 mL/min.

Preferably, said eluting in said step (b) is conducted at a pH range of 2 to 11.

Preferably, said eluting in said step (d) is conducted at a flow rate of 0.1 to 10 mL/min.

Preferably, said eluting in said step (d) is conducted at a pH range of 2 to 7.5.

Preferably, said hydrophilic interaction liquid chromatography (HILIC) column is an amide column.

Preferably, said reverse phase high performance liquid chromatography (RP-HPLC) column is a hydrophobic column.

More preferably, said hydrophobic column is a C4 column, C8 column, or C18 column.

DETAILED DESCRIPTION

Figure 1:
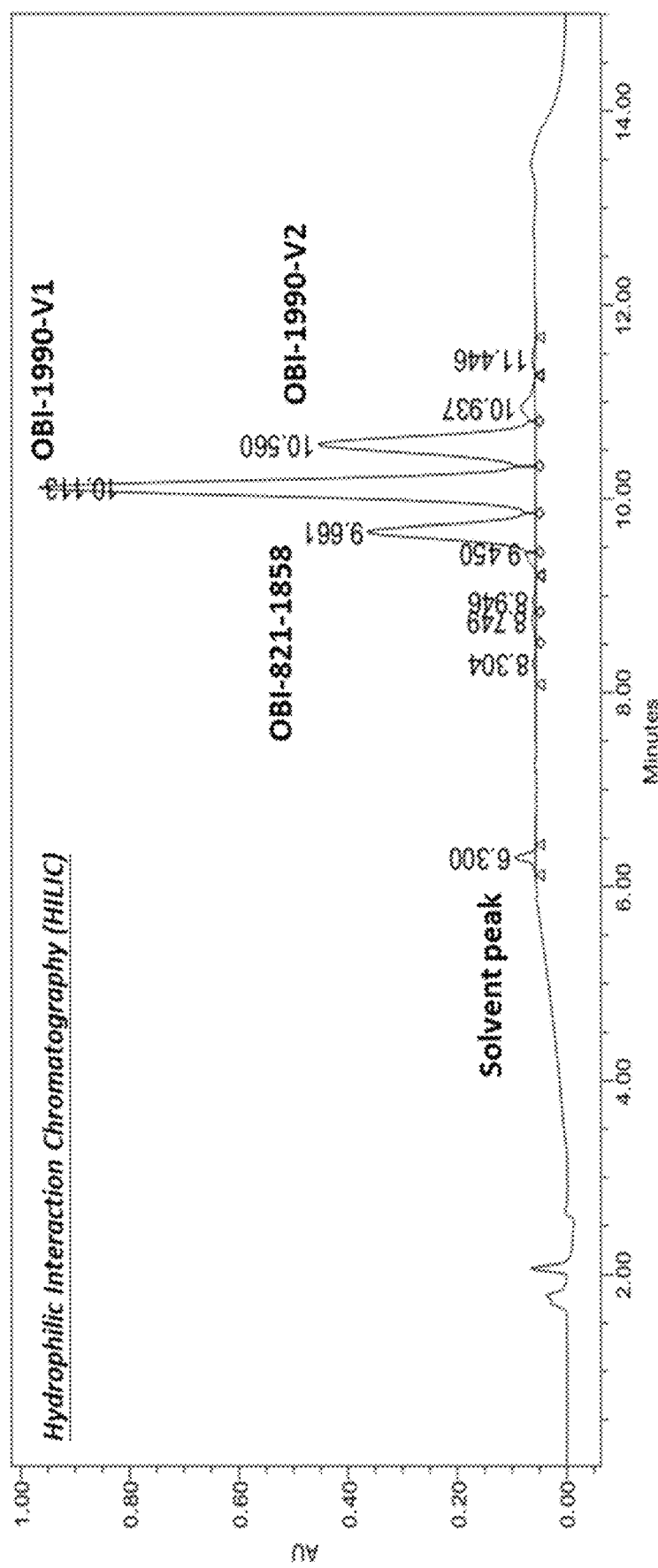
FIG. 1. OBI-821 hydrophilic interaction liquid chromatography (HILIC) ultraviolet (UV) chromatographram.

OBI-821 adjuvant substance (AS), a kind of saponin composition, is a plant-derived complex saponin from *Quillaja saponaria* and comprises six isomers sharing the following Formula (I):

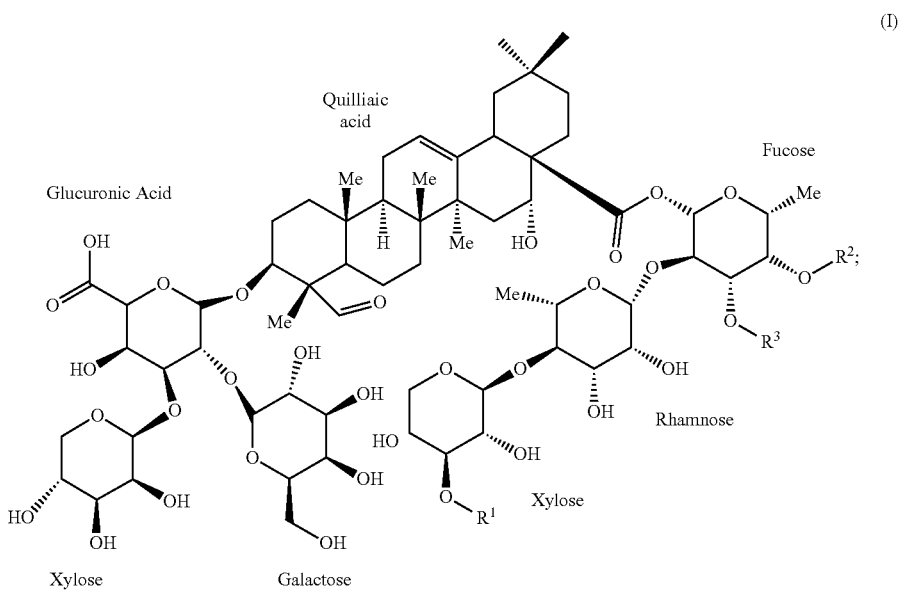

wherein $R^1$ is apiose, xylose, or H;
wherein $R^2$ and $R^3$ are independently hydrogen or a fatty acyl.

The six isomers are listed in the following Table 1 with reference name in this article. Among the six isomers, OBI-821-1990-V1 having a terminal apiose, OBI-821-1990-V2 having a terminal xylose and OBI-821-1858 having a disaccharide moiety (D-xylosyl-(1→4)-O-β-D-L-rhamnosyl-(1→4)) attached on the fucosyl residue instead of a trisaccharide moiety in OBI-821-1990 isomers are the major three components thereof. The three major components respectively have "A form" and "B form" regioisomers.

The number "1990" is the theoretically estimated molecular weight of OBI-821-1990-V1A, OBI-821-1990-V1B, OBI-821-1990-V2A, and OBI-821-1990-V2B. Likewise, the number "1858" is the theoretically estimated molecular weight of OBI-821-1858-A and OBI-821-1858-B.

TABLE 1

The six isomers of OBI-821 adjuvant substance (AS)

| Reference Name | $R^1$ | $R^2$ | $R^3$ |
|---|---|---|---|
| OBI-821-1990-V1A | β-D-Apiose | Fatty acyl | H |
| OBI-821-1990-V1B | β-D-Apiose | H | Fatty acyl |
| OBI-821-1990-V2A | β-D-Xylose | Fatty acyl | H |
| OBI-821-1990-V2B | β-D-Xylose | H | Fatty acyl |
| OBI-821-1858-A | H | Fatty acyl | H |
| OBI-821-1858-B | H | H | Fatty acyl |

There are total of six isomers found in OBI-821 adjuvant substance (AS). These six isomers can be classified into three groups, OBI-821-1990-V1, OBI-821-1990-V2 and OBI-821-1858. Each group contains two regioisomers that can be identified as group A and B. The nomenclature and physicochemical properties of OBI-821 adjuvant are summarized in Table 2.

TABLE 2

Nomenclature and physicochemical properties of OBI-821 adjuvant substance (AS)

| | |
|---|---|
| Chemical Name | (3β,4α,16α)-28-[[O-D-apio-β-D-furanosyl-(1→3)-O-β-D-xylopyranosyl-(1→4)-O-6-deoxy-α-L-mannopyranosyl-(1→2)-4-O-[5-[[5-(α-L-arabinofuranosyloxy)-3-hydroxy-6-methyl-1-oxooctyl]oxy]-3-hydroxy-6-methyl-1-oxooctyl]-6-deoxy-β-D-galactopyranosyl]oxy]-16-hydroxy-23,28-dioxoolean-12-en-3-ylO-β-D-galactopyranosyl-(1→2)-O-[β-D-xylopyranosyl-(1→3)]-β-D-glucopyranuronic acid |
| Chemical Formula | $C_{92}H_{148}O_{46}$ |
| Molecular Weight | 1990.1319 Da |
| Description | White to off-white powder |
| Signature Mass Spectrometry | m/z 2011.9 $[M + Na]^+$ |
| pKa | 2.68 ± 0.70 (from CAS 141256-04-4 of QS-21) |
| logP | 4.703 ± 1.065 (from CAS 141256-04-4 of QS-21) |
| Solubility | Soluble in water |

The manufacturing process of OBI-821 AS involves three purification stages (Stage I, II, and III). The initial content of OBI-821 found in Quil-A, key raw material, is typically not more than 3%. Stage I purification process increases OBI-821 contents to about 15% where the intermediates are identified as purified Quil-A (PQA). In Stage II process, OBI-821 contents are increased to about 0.2 g/g dried form with salt (about 50% main peak M.W. 1990, chromatographic purity by HPLC) where the intermediates are identified as crude OBI-821 (Crd-821). After the Stage III purification process, OBI-821 contents can be enriched to not less than 98% and are identified as OBI-821 AS.

Quil-A is commercially obtained from Brenntag Biosector A/S (Brenntag; Frederikssund, Denmark) which has been certified by the Denmark regulatory authorities for the use as food additives (Certificate No. 32119).

The first aspect of the present disclosure is directed to isolated saponin compounds from a saponin based adjuvant. The term "isolated" is referred to describe the saponin compound is substantially pure. More specifically, in an embodiment, the isolated saponin compound is free of impurity and other isomer of thereof. For example, in an embodiment, the isolater saponin compound is Compound 1990-VIA and it is free from Compound 1990-V2A, Compound 1990-V1B, Compound 1990-V2B, Compound 1858-A, and Compound 1858-B.

The second aspect of the present disclosure is about a saponin composition, comprising one or more of the aforesaid isolated compounds and a pharmaceutical acceptable carrier. The saponin composition might comprise two or more of the aforesaid isolated compounds in a ratio that is suitable for exhibiting adjuvant effects. The pharmaceutical acceptable carrier can be any carrier that is commonly used in the field.

In a preferable embodiment, the saponin composition comprises, by the total weight of the saponin composition, 75 to 90 wt % of a mixture of Compound 1990 and 10 to 25 wt % of a mixture of Compound 1858; wherein the mixture of Compound 1990 comprises Compound 1990-V1A, Compound 1990-V1B, Compound 1990-V2A, Compound 1990-V2B, or a mixture thereof; and the mixture of Compound 1858 comprises Compound 1858-A, Compound 1858-B, or a mixture thereof. In a more preferable embodiment, the saponin composition comprises, by the total weight of the saponin composition, 80 to 88 wt % of a mixture of Compound 1990 and 12 to 23 wt % of a mixture of Compound 1858.

In another preferable embodiment, the saponin composition comprises, by the total weight of the saponin composition: about 45 to 65 wt % of the Compound 1990-V1A. In a specific embodiment, the saponin composition comprises, by the total weight of the saponin composition, about 45 to 65 wt % of the Compound 1990-V1A; about 19.31 to 27.99 wt % of the Compound 1990-V2A; about 0.29 to 7.71 wt % of the Compound 1990-V1B; and about 0.11 to 3.11 wt % of the Compound 1990-V2B. In another specific embodiment, the saponin composition comprises, by the total weight of the saponin composition, about 49.26 to 63.42 wt % of the Compound 1990-V1A; about 19.31 to 27.99 wt % of the Compound 1990-V2A; about 0.29 to 7.71 wt % of the Compound 1990-V1B; and about 0.11 to 3.11 wt % of the Compound 1990-V2B.

The term of "evaluating the isomer composition of OBI-821" referred hereinafter is to separating OBI-821 by a method so that the three major components of OBI-821 can be separated and observed. This is essential to verify if a OBI-821 at issue does contain all the three major components as it might be a factor for the function of OBI-821 in enhancing antibody or cell-mediated immune response. The term of "evaluating the purity of OBI-821" referred hereinafter is to evaluate the content of impurity existing in a OBI-821 at issue. Preferably, the content of the impurity is less than 10 wt % in a OBI-821 at issue; that is, the purity of the OBI-821 is more than 90%. The term of "evaluating the quality of OBI-821" referred hereinafter is to evaluate both the existence of the three major components and the purity of a OBI-821 at issue.

In the third aspect of the present disclosure, a method for evaluating the isomer composition of a saponin composition by hydrophilic interaction liquid chromatography (HILIC) is provided. The method comprises: (a) applying the saponin composition to a hydrophilic interaction liquid chromatography (HILIC) column; (b) eluting said hydrophilic interaction liquid chromatography (HILIC) column with a mobile phase to obtain an eluate; and (c) obtaining a chromatogram of said eluate.

In a preferable embodiment, said mobile phase is applied in a gradient that the amount of said trifluoroacetic acid-water solution in said mobile phase varies from 0% (v/v) to 20% (v/v) while the amount of said acetonitrile in said mobile phase varies from 80% (v/v) to 100% (v/v) in 30 minutes; wherein said % (v/v) is based on the total volume of said mobile phase.

Said eluting can be conducted by a suitable flow rate depending on the conditions of the operation. Nevertheless, in a preferable embodiment, said eluting is conducted at a flow rate of 0.1 to 10 mL/min.

In a preferable embodiment, said column shall be conditioned by a buffer before the analysis is conducted. Additionally, in a preferable embodiment, said column shall be washed by a wash buffer after the analysis is completed. The buffer used for said condition could be a trifluoroacetic acid-water solution, acetonitrile, or a mixture thereof. Said wash buffer could be acetonitrile, water, or a mixture thereof. Preferably, said wash buffer is a mixture of acetonitrile and water of a suitable gradient.

In a preferable embodiment, said chromatogram would comprise three peaks respectively representing the three major components of the six isomers set forth above. Practically, the peak area of the three peaks can be calculated for preliminarily determining the purity of the OBI-821 at issue.

In the fourth aspect of the present disclosure, a method for evaluating the purity of a saponin composition by reversed-phase high-performance liquid chromatography (RP-HPLC) is provided. The method comprises: (a) applying the saponin composition to a reverse phase high performance liquid chromatography (RP-HPLC) column; (b) eluting said reverse phase high performance liquid chromatography (RP-HPLC) column with a mobile phase to obtain an eluate; and (c) obtaining a chromatogram of said eluate.

In a preferable embodiment, said mobile phase is applied in a gradient that the amount of said trifluoroacetic acid-water solution in said mobile phase varies from 20% (v/v) to 80% (v/v) while the amount of said acetonitrile in said mobile phase varies from 20% (v/v) to 80% (v/v) in 35 minutes; wherein said % (v/v) is based on the total volume of said mobile phase.

Said eluting can be conducted by a suitable flow rate depending on the conditions of the operation. Nevertheless, in a preferable embodiment, said eluting is conducted at a flow rate of 0.1 to 10 mL/min.

In a preferable embodiment, said chromatogram would comprise two peaks respectively representing the "A form" regioisomer and the "B form" regioisomer. Specifically, the peak representing the "A form" regioisomer would be a combination of OBI-821-1990-V1A, OBI-821-1990-V2A, and OBI-821-1858-A; the peak representing the "B form" regioisomer would be a combination of OBI-821-1990-V1B, OBI-821-1990-V2B, and OBI-821-1858-B. In a preferable embodiment, the peak area of said two peaks can be calculated for determining the purity of the OBI-821 at issue.

In the fifth aspect of the present disclosure, a method for evaluating the quality of a saponin composition is provided. The method is performed by HILIC and RP-HPLC in tandem. Basically, a saponin composition is applied for the method for evaluating the isomer composition of a saponin composition of the third aspect of the present disclosure and then the obtained fraction was applied for the method for evaluating the purity of OBI-821 of the fourth aspect of the present disclosure.

Specifically, the method comprises (a) applying a saponin composition to a hydrophilic interaction liquid chromatography (HILIC) column; (b) eluting said hydrophilic interaction liquid chromatography (HILIC) column with a first mobile phase to collect a first eluate; (c) applying a fraction of said first eluate to a reverse phase high performance liquid chromatography (RP-HPLC) column; (d) eluting said reverse phase high performance liquid chromatography (RP-HPLC) column with a second mobile phase to collect a second eluate; and (e) obtaining a chromatogram of said second eluate.

Preferably, the conditions including column, mobile phase, flow rate, etc. of the hydrophilic interaction liquid chromatography (HILIC) and the reverse phase high performance liquid chromatography (RP-HPLC) are the same as set forth in the previous paragraphs.

In a preferable embodiment, fraction of said first eluate representing any one of the three major components of the six isomers is applied for said reverse phase high performance liquid chromatography (RP-HPLC) column in said step (c) so that the "A form" regioisomer and the "B form" regioisomer of fraction can be separated.

In a preferable embodiment, three fractions respectively representing the three major components of the six isomers are collected for said reverse phase high performance liquid chromatography (RP-HPLC) column in said step (c) so that the "A form" regioisomer and the "B form" regioisomer of the each three major components can be separated. Accordingly, three chromatograms can be obtained with each of them having one peak representing the "A form" regioisomer and one peak representing the "B form" regioisomer. Calculating the peak area of the two peaks of the three chromatograms obtained is able to provide the contents of each six isomers of the OBI-821 at issue.

EXAMPLES

Example 1: Separating OBI-821 Adjuvant by HILIC

This experiment was conducted to separate OBI-821 adjuvant so that the three major components of the six isomers could be observed. The analytical methods and conditions are summarized in the following Table 3 and Table 4. 1.0 to 2.0 mg of test sample was dissolved in a blank buffer (80% (v/v) acetonitrile in deionized water) to prepare OBI-821 solution (500 µg/mL). Then, the OBI-821 solution was injected into a WATERS)(Bridge amide column (Waters Corporation, Part No. 186004896). The mobile phase of the HILIC was a mixture of eluent A and eluent B. Eluent A was 0.1% (v/v) trifluoroacetic acid dissolved in deionized water (DI water) and eluent B was acetonitrile. The gradient of the mobile phase was set as the elution program shown in Table 4 as follows.

TABLE 3

Conditions of HILIC

| | |
|---|---|
| Mobile Phase | Eluent A: 0.1% (v/v) TFA in DI water |
| | Eluent B: ACN |
| Column | WATERS XBridge amide column |
| | (Part No. 186004896) |
| Flow Rate | 1.0 mL/min |
| Equilibrium Program | Condition column with 18% eluent A and 82% eluent B for 1 hour before analysis |
| Injection Volume | 50 μL |
| Detection | ultraviolet (214 nm) |
| Data Acquisition Time | 30 min |

TABLE 4

Elution program of HILIC

| Time (min) | Eluent A (%) | Eluent B (%) |
|---|---|---|
| 0 | 18.0 | 82.0 |
| 18 | 19.0 | 81.0 |
| 25 | 19.0 | 81.0 |
| 26 | 18.0 | 82.0 |
| 30 | 18.0 | 82.0 |

Data Processing:
1. Process chromatograms at 214 nm. Integrate all the peaks and record the retention time, peak area (area under curve), and area % of all the peaks. (Note: please avoid integrating solvent peaks from Blank). The area % can be understood as wt % (wt/wt).
2. Calculation of relative retention time (RRT)
    RRT is the ratio of retention time of the peak over the retention time of peak 1990-V1. The retention time of 1990-V1 is defined by average retention time of main peak in OBI-821 solution.

$$RRT = RT_{peak}/RT_{1990-Api}$$

3. Peak identification
    Three OBI-821 components (1858, 1990-V1 and 1990-V2) are identified by the relative retention time (RRT) shown in Table 5 as follows:

TABLE 5

Relative retention time of 1858 isomer, 1990-V1 isomer and 1990-V2 isomer of HILIC

| Isomer Name | RRT for Identification |
|---|---|
| 1990-V1 (terminal apiose) | 1.00 ± 0.1 |
| 1858 | 0.93 ± 0.1 |
| 1990-V2 (terminal xylose) | 1.07 ± 0.1 |

Data Analysis:
1. System Suitability Test (SST)
    The result of SST is obtained from injection of OBI-821 solution. Calculate the relative standard deviation (RSD %) of RT and peak area of 1990-Api. The acceptance criteria of RT and peak area should be less than 2%.
2. Sugar isomer distribution
    Sugar isomer distribution is determined by the peak area of peak.
    1858(%)=peak area of 1858/sum of peak area of 3 peaks (1858, 1990-V1 and 1990-V2)×100%
    1990-V1(%)=peak area of 1990-V1/sum of peak area of 3 peaks (1858, 1990-V1 and 1990-V2)×100%
    1990-V2(%)=peak area of 1990-V2/sum of peak area of 3 peaks (1858, 1990-V1 and 1990-V2)×100%

Average the results and calculate the relative standard deviation (% RSD). Express final result as mean water content±standard deviation.

As shown in FIG. 1, the chromatographram of OBI-821 showed three major peaks respectively at 9.661 minute (hereinafter Peak 1; OBI-821-1858), 10.113 minute (hereinafter Peak 2; OBI-821-1990-V1) and 10.560 minute (hereinafter Peak 3; OBI-821-1990-V2) of retention time. There was also another peak at 6.300 minute of retention time, which would be the solvent peak of the HILIC.

Figure 2:
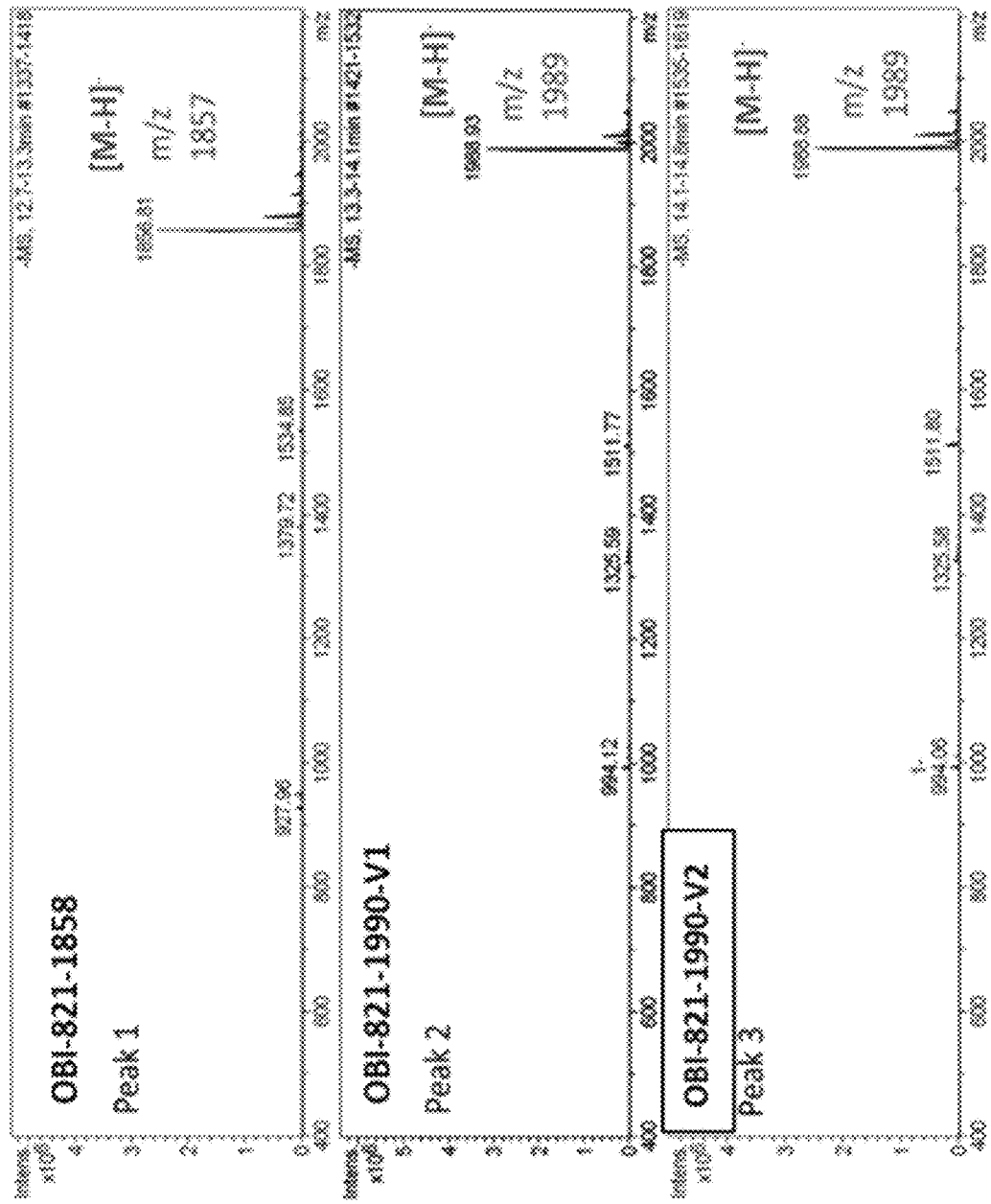
FIG. 2. OBI-821 Negative ESI MS spectra of the Peak 1 fraction (1858 compound, top), Peak 2 fraction (1990-V1 compound, middle) and Peak 3 fraction (1990-V2 compound, bottom) collected from hydrophilic interaction liquid chromatography (HILIC) ultraviolet (UV) chromatographram.

In order to further identify the eluents of the aforesaid three major peaks, the fractions of the aforesaid three peaks of OBI-821 were collected and examined by negative ESI MS. As shown in FIG. 2, m/z 1989 was observed for OBI-821-1990-V1 (peak 2) and -V2 (peak 3); m/z 1857 was observed for −1858 (peak 1). These m/z results are consistent with the theoretical molecular weight 1990.13192 ($C_{92}H_{148}O_{46}$) and 1858.0173 ($C_{87}H_{140}O_{42}$), respectively.

Figure 3A:
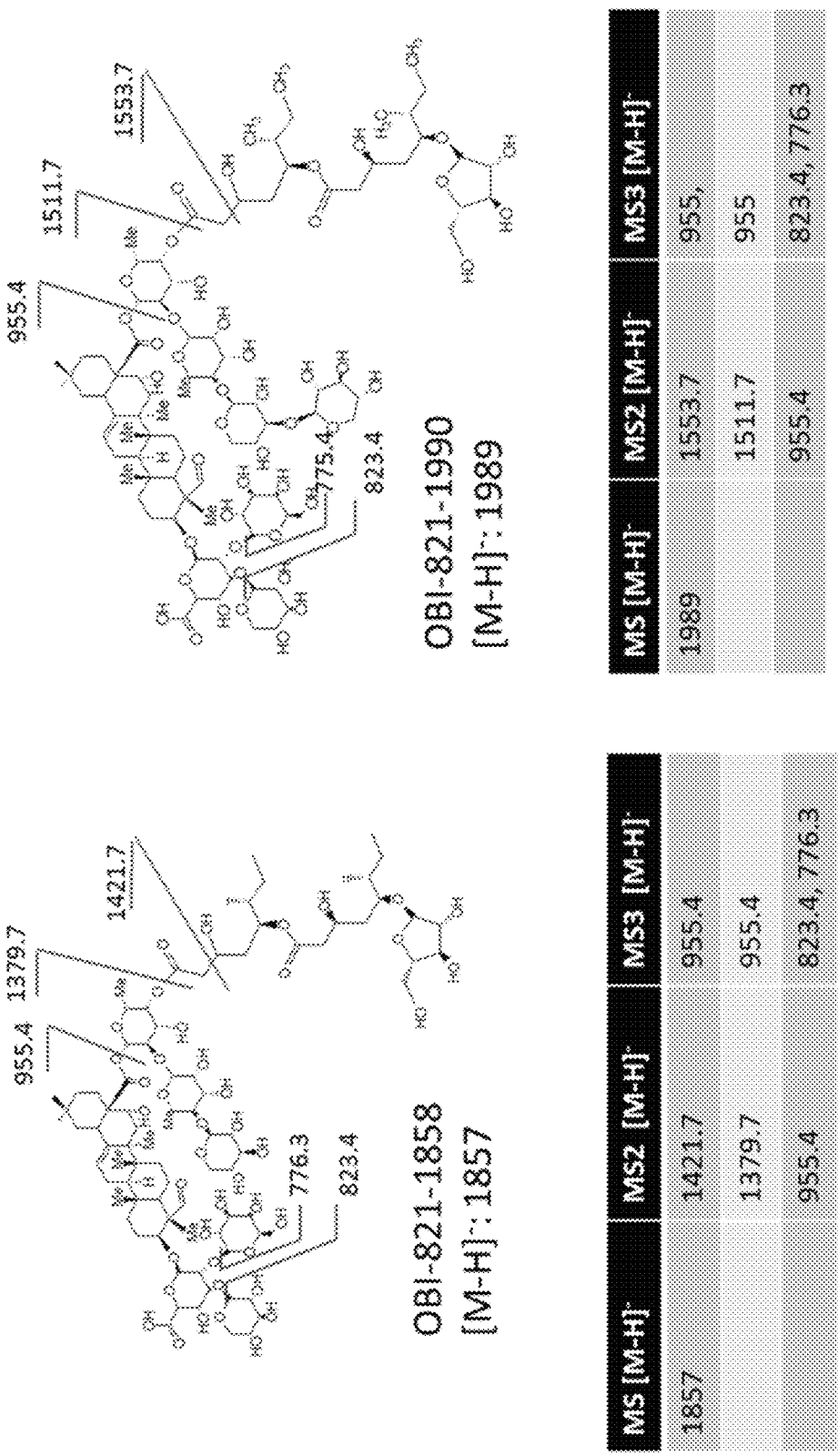
FIG. 3. (A) Structure of 1858 compound (left) and 1990 compound (right) and their tandem MS fragmentation ion from OBI-821 and (B) MS/MS spectra of 1990 compound (top) and 1858 compound (bottom).
Figure 3B:
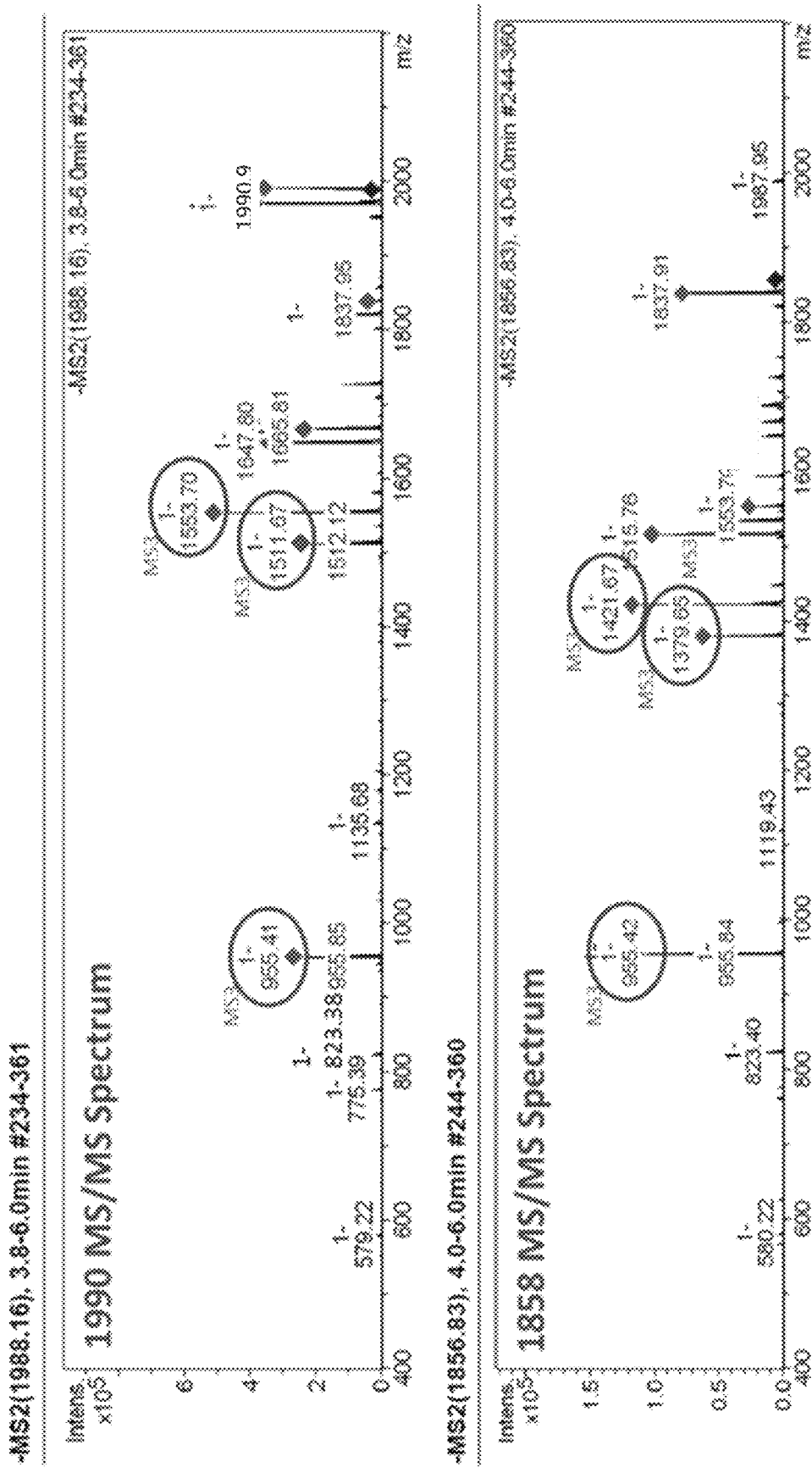

To confirm the structure of OBI-821 isomers, the eluent of the three peaks in ESI MS were further applied for structural analysis via directed infusion MS/MS and MS/MS/MS analysis. The tandem MS structural information is summarized in FIG. 3 (A). The MS/MS spectra are shown in FIG. 3 (B), the assigned mass peak in the figures have been selected for MS/MS/MS analysis. From the tandem mass spectra, it showed the corresponding structure relation between fragment ions and the parent ion.

Then, High performance anion exchange chromatography with pulsed amperometric detection (HPAEC-PAD) monosaccharide analysis (Thermo Fisher Scientific, Dionex ICS-5000 with CarboPac PA1 column (Part. No. 035391, 4×250 mm)) was conducted to further distinguish the identities of the three fractions. OBI-1990-V1, -V2, and -1858 were collected from HILIC and were concentrated by rotary vapor. The concentrated OBI-1990-V1, -V2, and -1858 were hydrolyzed by 4 M TFA under 100° C. for 4 hour and lyophilized. After lyophilization, OBI-1990-V1, -V2, and -1858 were reconstituted by DI water and analyzed by High performance anion exchange chromatography with pulsed amperometric detection (HPAEC-PAD). 200 mM sodium hydroxide was used as mobile phase A and DI water was used as mobile phase B. 100 mM sodium hydroxide with 500 mM sodium acetate was used as mobile phase C.

The initial composition of mobile phase was held at 91% mobile phase A and 9% mobile phase B for 10 min. Then switched to 90% mobile phase A and 10% mobile phase C and followed by a linearly gradient to 60% mobile phase A and 40% mobile phase C in 10 min. Then carried out wash-step by 100% mobile phase A for 20 min.

Figure 4:
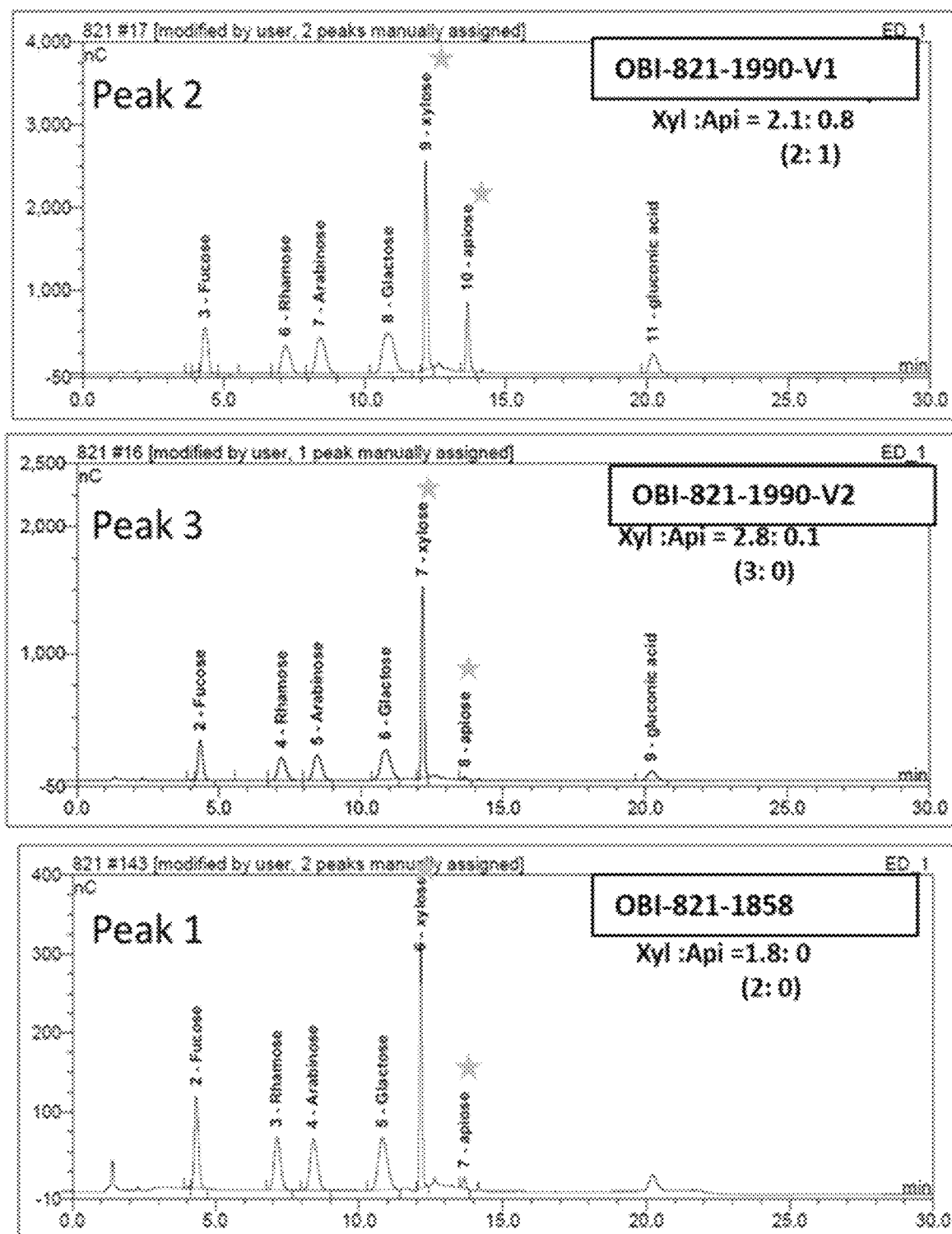
FIG. 4. High performance anion exchange chromatography with pulsed amperometric detection (HPAEC-PAD) monosaccharide analysis of Peak 2 fraction (1990-V1 compound, top), Peak 3 fraction (1990-V2 compound, middle) and Peak 1 fraction (1858 compound, bottom) collected from hydrophilic interaction liquid chromatography (HILIC) ultraviolet (UV) chromatographram.

According to the results shown in FIG. 4 and Table 1, the three eluents all had one fucose, one hamnose, one galactose, one glucuronic acid and one arabinose but were different in the numbers of xylose and apiose. Peak 1 fraction had 2 xyloses but no apiose. Peak 2 fraction had 2 xyloses and 1 apiose. Peak 3 fraction had 3 xyloses and 0 apiose. Accordingly, the three fractions were identified as the OBI-821-1858 isomer, OBI-821-1990-V1 isomer and OBI-821-1990-V2 isomer respectively. That is to say, the HILIC analysis conducted in this experiment was capably of separating the three major components of the six isomers of OBI-821. In other words, the three major components of OBI-821 could be clearly observed through the aforesaid HILIC analysis.

TABLE 6

Monosaccharide composition molar ratio of peak fractions collected from HILIC.

| Monosaccharide composition molar ratio | Peak 1 | Peak 2 | Peak 3 |
|---|---|---|---|
| Fucose | (1)* | (1) | (1) |
| Rhamnose | (1) | (1) | (1) |
| Galactose | (1) | (1) | (1) |
| Glucuronic acid | (1) | (1) | (1) |
| Arabinose | (1) | (1) | (1) |
| Xylose | 1.8 (2) | 2.1† (2) | 2.8 (3) |
| Apiose | 0 (0) | 0.8 (1) | 0.1 (0) |

*Theoretical value estimated from structure.
†Calculated value from standard curve.

Example 2: Identifying the Regioisomers of OBI-821 Adjuvant by RP-HPLC

In this experiment, OBI-821 was separated by reverse phase high-performance liquid chromatography (RP-HPLC) in order to identify the regioisomers thereof. As known in the field, the OBI-821 has A form regioisomer with the acyl group bonded at the 4-hydroxyl position of the fucose and B form regioisomer with the acyl group at the 3-hydroxyl position. The conditions of RP-HPLC were listed in the following Table 7 and Table 8. Briefly, test sample was dissolved in a formulation buffer (1.25 mg/mL) and injected into a YMC-Pack C4 column (Part No. BU30S05-2546WT, 5 μm, 4.6×250 mm) and the column was eluted by a mobile phase comprising 0.1% TFA in water/acetonitrile gradient in 15 minutes. The eluate was then detected by ultraviolet of 214 nm.

TABLE 7

Conditions of RP-HPLC

| | |
|---|---|
| Mobile Phase | Eluent A: 0.1% (v/v) TFA in DI water |
| | Eluent B: 0.1% (v/v) TFA in ACN |
| Column | YMC-Pack C4 column (Part No. BU30S05-2546WT) |
| Flow Rate | 1.0 mL/min |
| Formulation Buffer | Weigh 0.62 g of Monobasic Sodium phosphate, dehydrate, 0.98 g of dibasic sodium phosphate, anhydrous, 55.23 g of trehalose dihydrate and 4.40 g of sodium chloride (NaCl). Dissolve with 900 mL of DI water and adjust pH to 6.8. Then dilute to 1 L and filtrate the solution with 0.22 μm Nylon membrane or less pore size membrane filter. |
| Equilibrium Program | Condition column with 80% ACN and 20% DI water for 1 hour before analysis |
| Injection Volume | 100 μL |
| Detection | Ultraviolet (214 nm) |
| Data acquisition time | 35 min |

TABLE 8

Elution program of RP-HPLC

| Time (min) | Eluent A (%) | Eluent B (%) |
|---|---|---|
| 0 | 75 | 25 |
| 15 | 25 | 75 |
| 20 | 20 | 80 |
| 30 | 75 | 25 |
| 35 | 75 | 25 |

Data Processing:
1. Process chromatograms at 214 nm. The Integration parameters are listed as follows:
   (a) Peak width: 30
   (b) Threshold: 50.0
   (c) Minimum peak height: 2000
   (d) Integration time: 6-17 min
2. Peak definition
   In YMC-Pack C4 chromatography, OBI-821 is composed of Major peak and Minor peak. Record the retention time of Major peak, and Minor peak. Minor peak relative retention time (RRT) to Major peak should be within 0.95-0.97.

Data Analysis:
1. System suitability
   Calculate the average retention time and peak area and relative standard deviation (RSD). The RSD of RT and peak area should be less than 2%. The peaks of SST should also meet the criteria:
   USP tailing: 0.5-2.0
   USP plate count: ≥8000
   Resolution: ≥1.8
2. Identification of OBI-821:
   Record the peak retention time of test sample. The retention time of test sample should be corresponding to the retention time of OBI-821 reference standard. The retention time difference from the standard should be within 2%.
3. Determination the purity and impurity of OBI-821
   The purity and impurity is determined by the peak area analysis of recording peak area % as follows:

Purity (%)=($A_{OBI-821}/A_{total\ peaks}$)

Single impurity (%)=($A_{single\ impurity\ peak}/A_{total\ peaks}$)

Total impurity (%)=($A_{total\ impurity\ peaks}/A_{total\ peaks}$)

$A_{OBI-821}$=Sum of peak area from Major peak and Minor peak of test sample $A_{single\ impurity\ peak}$=The peak area from single impurity peak except solvent peaks $A_{total\ impurity\ peaks}$=Sum of peak area from every single impurity peaks except solvent peaks $A_{total\ peaks}$=Peak Area of all peaks except solvent peaks
Average the value of purity (%) and impurity (%) of each test sample.

Figure 5:
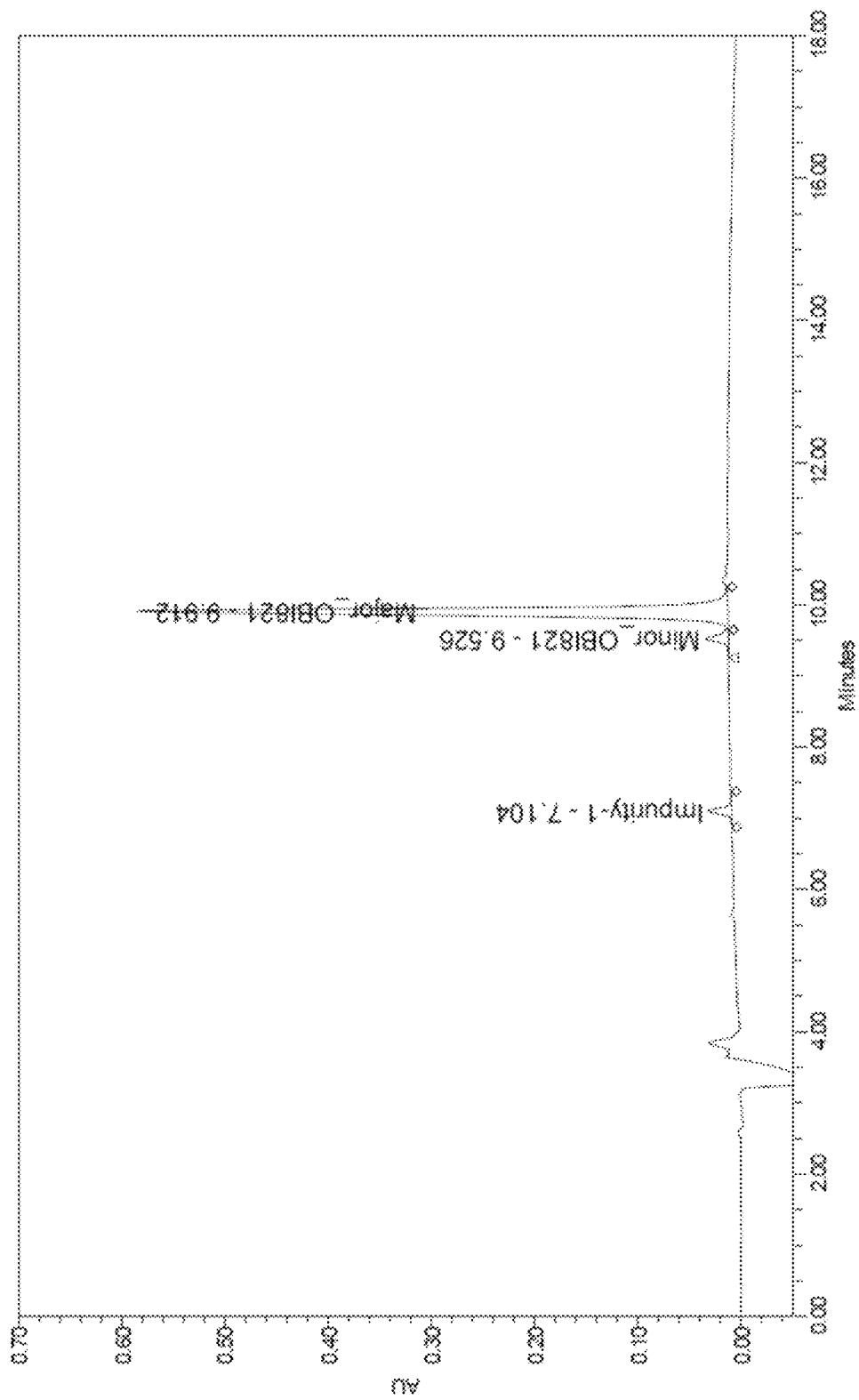
FIG. 5. OBI-821 Reverse phase high performance liquid chromatography (RP-HPLC) chromatogram.

The result are shown in FIG. 5. There was a major peak at 9.912 minute of retention time and a minor peak at 9.526 minute. The major peak represented the A form regioisomer including OBI-821-1858-A, OBI-821-1990-V1A, and OBI-821-1990-V2A. The minor peak represented the B form regioisomer including OBI-821-1858-B, OBI-821-1990-V1B, and OBI-821-1990-V2B. A further peak at 7.104 minute was identified as impurity. Thus, the result proved that the RP-HPLC of this experiment is capable of separating the two forms of regioisomers of OBI-821 so that the existence and content thereof can be clearly observed.

Additionally, the relative retention time of the aforesaid impurity peak, major peak and minor peak was calculated by using the retention time of major peak as standard (Table 9). Furthermore, the purity was about 96.72%. Together with the results obtained, the RP-HPLC of the present disclosure was useful in determining the purity of the OBI-821 at issue.

TABLE 9

| | Quantified data of the chromatogram of OBI-821 | | | | |
|---|---|---|---|---|---|
| | Peak Name | RT | Area | % Area | Height |
| 1 | Impurity | 7.104 | 138133 | 3.28 | 22968 |
| 2 | Minor peak | 9.526 | 144117 | 3.43 | 22138 |
| 3 | Major peak | 9.912 | 3924465 | 93.29 | 571460 |

Example 3: Identifying the Six Isomers of OBI-821 by Tandem Combination of HILIC and RP-HPLC The studies described in Example 1 provided evidences that the present HILIC analysis is able to separate the three major components of OBI-821 isomers. The studies in Example 2 confirmed the present RP-HPLC analysis is useful for observing the regioisomers of OBI-821. Thus, it would be reasonable to combine the present HILIC analysis and the RP-HPLC analysis in tandem so that the fractions collected in the HILIC analysis could be further divided into A form regioisomer and B form regioisomer of each fractions. Subsequently, the six isomers of OBI-821 could be separated and the contents thereof could be calculated.

In this experiment, six adjuvant substance samples were applied for HILIC analysis as recited in the aforesaid Example 1 to collect three fractions representing the three major components. Afterwards, each fraction was respectively subject to RP-HPLC analysis as disclosed in the aforesaid Example 2 to separate the regioisomers thereof. Thus, in the end of the analysis, six isomers were expected to be obtained from each OBI-821 sample. The peak area of the six peaks of each sample was determined for the calculation of the contents of each isomer. The results of OBI-821 AS (Adjuvant Substance) and OBI-821 AP (Adjuvant Product) are shown in Table 10 and Table 11.

TABLE 10

The contents of each isomer of the OBI-821 AS lots.

| OBI-821 AS Lot No. | 1990-V1A | 1990-V2A | 1990-V1B | 1990-V2B | 1858-A | 1858-B | Note |
|---|---|---|---|---|---|---|---|
| P0001N0002 | 63.42% | 23.19% | 0.29% | 0.11% | 12.93% | 0.06% | 1990-V1A highest |
| P0001N0001 | 50.80% | 28.91% | 0.60% | 0.34% | 17.10% | 0.20% | 1990-V2A highest |
| 120531 | 54.03% | 22.61% | 0.51% | 0.21% | 21.25% | 0.20% | 1858-A highest |
| 080801 | 55.10% | 22.13% | 4.58% | 1.84% | 13.91% | 1.16% | 1858-B highest |
| 05371002 | 62.36% | 23.36% | 0.31% | 0.12% | 13.78% | 0.07% | |
| 05371001 | 54.18% | 27.99% | 0.31% | 0.11% | 17.34% | 0.07% | |

TABLE 11

The contents of each isomer of the OBI-821 AP lots.

| OBI-821 AP Lot No. | 1990-V1A | 1990-V2A | 1990-V1B | 1990-V2B | 1858-A | 1858-B | Note |
|---|---|---|---|---|---|---|---|
| 301525 | 60.55% | 21.91% | 3.84% | 1.19% | 11.94% | 0.57% | 1990-V1A highest |
| 301421 | 49.36% | 27.99% | 3.11% | 3.11% | 15.29% | 1.14% | 1990-V2A highest |
| 14001 | 49.26% | 20.27% | 4.45% | 1.83% | 20.92% | 1.89% | 1858-A highest |
| 13001 | 49.91% | 19.31% | 7.71% | 2.98% | 15.81% | 2.44% | 1858-B highest |
| 16002 | 58.43% | 21.51% | 4.81% | 2.01% | 12.20% | 1.03% | |
| 11001 | 55.10% | 22.13% | 4.58% | 1.84% | 13.91% | 1.16% | |
| 09001 | 56.38% | 21.13% | 3.95% | 1.48% | 14.85% | 1.04% | |

※OBI-821 AP (Adjuvant Product) is the lyophilization formulation of OBI-821 AS.

The reported percentage is normalized and calculated from chromatographic data of HILIC and RP-HPLC. Three major isomers, OBI-821-1990-V1A, -V2A, and 1858-A, account for over 90% of OBI-821 adjuvant by chromatographic composition. These three major isomers are found to be formed from fatty acyl substituent attached to the 4-hydroxyl group of the fucose residue. Among the six isomers, OBI-821-1990-V1A accounts for 49 to 63% and is the primary isomer for OBI-821 adjuvant.

Unless defined otherwise, all technical and scientific terms and any acronyms used herein have the same meanings as commonly understood by one of ordinary skill in the art in the field of this invention. Although any compositions, methods, kits, and means for communicating information similar or equivalent to those described herein can be used to practice this invention, the preferred compositions, methods, kits, and means for communicating information are described herein.

All references cited herein are incorporated herein by reference to the full extent allowed by law. The discussion of those references is intended merely to summarize the assertions made by their authors. No admission is made that any reference (or a portion of any reference) is relevant prior art. Applicants reserve the right to challenge the accuracy and pertinence of any cited reference.

The invention claimed is:

1. A saponin composition, comprising, by the total weight of the saponin composition:
    45 to 65 wt % of the Compound 1990-V1A;
    19.31 to 27.99 wt % of the Compound 1990-V2A;
    0.29 to 7.71 wt % of the Compound 1990-V1B;
    0.11 to 3.11 wt % of the Compound 1990-V2B;
    11.94 to 21.25 wt % of the Compound 1858-A;
    0.06 to 2.44 wt % of the Compound 1858-B; and
    a pharmaceutically acceptable carrier,
    wherein the mixture of Compound 1990 comprises Compound 1990-V1A, Compound 1990-V1B, Compound 1990-V2A, Compound 1990-V2B, or a mixture thereof; and the mixture of Compound 1858 comprises Compound 1858-A, Compound 1858-B, or a mixture thereof;
    wherein the Compound 1990-V1A, Compound 1990-V1B, Compound 1990-V2A, Compound 1990-V2B, Compound 1858-A, Compound 1858-B, are of the following formula respectively:

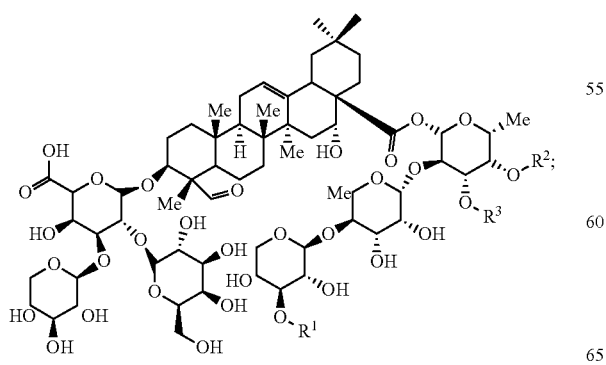

(I)

Compound 1990-V1A: $R^1$ is β-D-Apiose, $R^2$ is

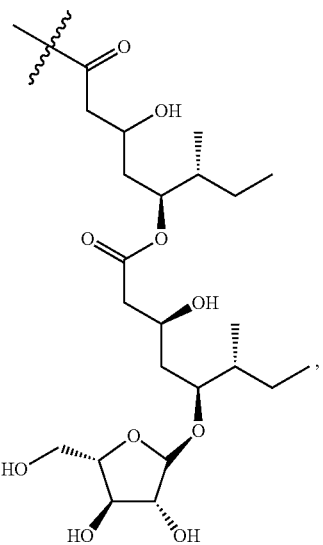

and $R^3$ is H;

Compound 1990-V1B: $R^1$ is β-D-Apiose, $R^2$ is H, and $R^3$ is

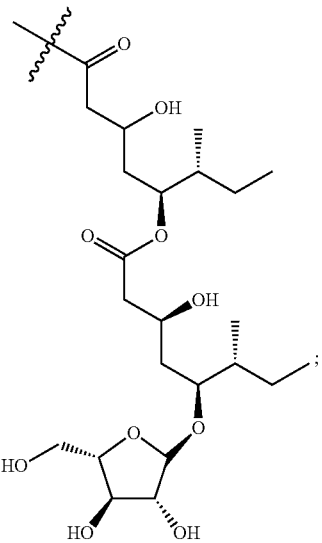

Compound 1990-V2A: R¹ is β-D-Xylose, R² is

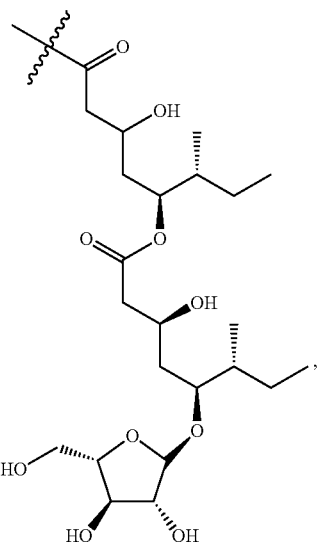

and R³ is H;

Compound 1990-V2B: R¹ is β-D-Xylose, R² is H, and R³ is

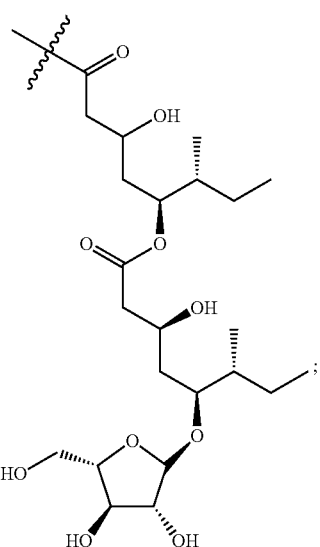

Compound 1858-A: R¹ is H, R² is

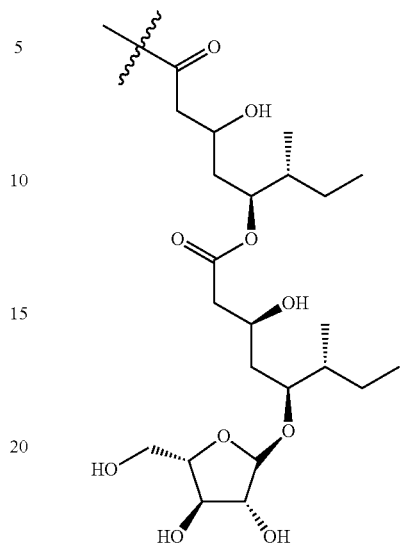

and R³ is H;
and

Compound 1858-B: R¹ is H, R² is H and R³ is

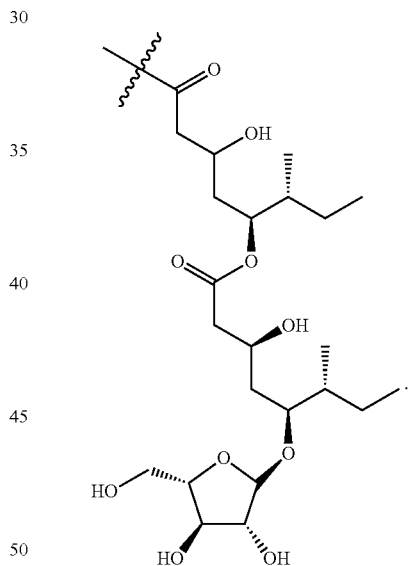

2. A method for evaluating the isomer composition of a saponin composition of claim 1, comprising:
(a) applying the saponin composition to a hydrophilic interaction liquid chromatography (HILIC) column;
(b) eluting said hydrophilic interaction liquid chromatography (HILIC) column with a first mobile phase to obtain a first eluate; and
(c) obtaining a chromatogram of said first eluate;
wherein said first mobile phase comprises a trifluoroacetic acid-water solution and acetonitrile.

3. The method of claim 2, wherein said eluting is conducted at a flow rate of 0.1 to 10 mL/min.

4. The method of claim 2, wherein said hydrophilic interaction liquid chromatography (HILIC) column is an amide column.

5. The method of claim 2, wherein said chromatogram is obtained by ultraviolet detection.

6. A method for evaluating the purity of a saponin composition of claim 1, comprising:
   (a) applying the saponin composition to a reverse phase high performance liquid chromatography (RP-HPLC) column;
   (b) eluting said reverse phase high performance liquid chromatography (RP-HPLC) column with a mobile phase to obtain an eluate; and
   (c) obtaining a chromatogram of said eluate;
   wherein said mobile phase comprises a trifluoroacetic acid-water solution and a trifluoroacetic acid-acetonitrile solution.

7. The method of claim 6, wherein said eluting is conducted at a flow rate of 0.1 to 10 mL/min.

8. The method of claim 6, wherein said reverse phase high performance liquid chromatography (RP-HPLC) column is a hydrophobic column.

9. The method of claim 8, wherein said hydrophobic column is a C4 column, C8 column, or C18 column.

10. The method of claim 6, wherein said chromatogram is obtained by ultraviolet detection.

11. A method for evaluating the quality of a saponin composition of claim 1, comprising:
    (a) conducting the method of claim 2, and further
    (b) applying a fraction of said first eluate to a reverse phase high performance liquid chromatography (RP-HPLC) column;
    (c) eluting said reverse phase high performance liquid chromatography (RP-HPLC) column with a second mobile phase to collect a second eluate; and
    (d) obtaining a chromatogram of said second eluate;
    wherein said first mobile phase comprises a trifluoroacetic acid-water solution and acetonitrile; and
    wherein said second mobile phase comprises a trifluoroacetic acid-water solution and a trifluoroacetic acid-acetonitrile solution.

12. The method of claim 11, wherein said eluting is conducted at a flow rate of 0.1 to 10 mL/min.

13. The method of claim 11, wherein said hydrophilic interaction liquid chromatography (HILIC) column is an amide column.

14. The method of claim 11, wherein said reverse phase high performance liquid chromatography (RP-HPLC) column is a hydrophobic column.

15. The method of claim 14, wherein said hydrophobic column is a C4 column, C8 column, or C18 column.

\* \* \* \* \*